US011020289B2

(12) United States Patent
Carla et al.

(10) Patent No.: US 11,020,289 B2
(45) Date of Patent: Jun. 1, 2021

(54) ABSORBENT STRUCTURE

(71) Applicant: The Procter & Gamble Company, Cincinnati, OH (US)

(72) Inventors: Vito Carla, Cincinnati, OH (US); Jan Claussen, Wiesbaden (DE); Christopher Philip Bewick-Sonntag, Cincinnati, OH (US); Wade Monroe Hubbard, Jr., Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 477 days.

(21) Appl. No.: 15/344,239

(22) Filed: Nov. 4, 2016

(65) Prior Publication Data

US 2017/0119595 A1 May 4, 2017

Related U.S. Application Data

(60) Provisional application No. 62/251,049, filed on Nov. 4, 2015.

(51) Int. Cl.
*A61F 13/53* (2006.01)
*A61F 13/534* (2006.01)
*A61F 13/15* (2006.01)

(52) U.S. Cl.
CPC ........ *A61F 13/53* (2013.01); *A61F 13/15203* (2013.01); *A61F 13/534* (2013.01); *A61F 2013/15373* (2013.01); *A61F 2013/530817* (2013.01); *A61F 2013/530839* (2013.01); *A61F 2013/530905* (2013.01)

(58) Field of Classification Search
CPC .. A61F 13/15203; A61F 13/53; A61F 13/534; A61F 2013/15373; A61F 2013/530817
See application file for complete search history.

(56) References Cited

U.S. PATENT DOCUMENTS

| 3,884,000 | A | 5/1975 | Faleij |
| 3,908,645 | A | 9/1975 | Sandvig |
| 3,982,374 | A | 9/1976 | Schaefer |
| 3,994,298 | A | 11/1976 | Des Marais |
| 4,026,292 | A | 5/1977 | Hutchins et al. |
| 4,055,184 | A | 10/1977 | Karami |

(Continued)

FOREIGN PATENT DOCUMENTS

| CA | 2250138 | 3/1997 |
| EP | 0278476 | 2/1988 |

(Continued)

OTHER PUBLICATIONS

PCT International Search Report, PCT/US2015/037943, dated Aug. 26, 2015, 9 pages.

(Continued)

*Primary Examiner* — Michele M Kidwell
(74) *Attorney, Agent, or Firm* — William E. Gallagher

(57) ABSTRACT

An absorbent product comprising a topsheet, a backsheet, and an absorbent core, the absorbent core comprising an absorbent structure comprising one or more stratum comprising one or more enrobeable elements, wherein a smooth transition zone is exhibited between an acquisition portion of the absorbent structure and a storage portion of the absorbent structure.

11 Claims, 6 Drawing Sheets

(56) References Cited

U.S. PATENT DOCUMENTS

| | | |
|---|---|---|
| 4,061,145 A | 12/1977 | DesMarais |
| 4,606,958 A | 8/1986 | Haq et al. |
| 4,664,662 A | 5/1987 | Webster |
| 4,758,466 A | 7/1988 | Dabi et al. |
| 4,865,596 A | 9/1989 | Weisman et al. |
| 5,221,726 A | 6/1993 | Dabi et al. |
| 5,260,345 A | 11/1993 | DesMarais et al. |
| 5,328,935 A | 7/1994 | Van Phan et al. |
| 5,331,015 A | 7/1994 | DesMarais et al. |
| 5,338,766 A | 8/1994 | Phan et al. |
| 5,387,207 A | 2/1995 | Dyer et al. |
| 5,536,264 A | 7/1996 | Hsueh et al. |
| 5,560,878 A | 10/1996 | Dragoo et al. |
| 5,713,881 A | 2/1998 | Rezai |
| 5,722,482 A | 3/1998 | Buckley |
| 5,817,704 A | 10/1998 | Shiveley et al. |
| 5,868,724 A | 2/1999 | Dierckes, Jr. et al. |
| 5,948,829 A | 9/1999 | Wallajapet et al. |
| 6,083,211 A | 7/2000 | DesMarais |
| 6,107,538 A | 8/2000 | Young et al. |
| 6,174,929 B1 | 1/2001 | Hahnle et al. |
| 6,183,587 B1 | 2/2001 | McFall et al. |
| 6,203,654 B1 | 3/2001 | McFall et al. |
| 6,261,679 B1 | 7/2001 | Chen et al. |
| 6,277,104 B1 | 8/2001 | Lasko et al. |
| 6,316,688 B1 | 11/2001 | Hammons et al. |
| 6,372,953 B1 | 4/2002 | Young et al. |
| 6,399,854 B1 | 6/2002 | Vartiainen |
| 6,410,820 B1 | 6/2002 | McFall et al. |
| 6,426,445 B1 | 7/2002 | Young et al. |
| 6,455,600 B1 | 9/2002 | Hahnle et al. |
| 6,475,199 B1 | 11/2002 | Gann et al. |
| 6,525,106 B1 | 2/2003 | DesMarais et al. |
| 6,551,295 B1 | 4/2003 | Schmidt et al. |
| 6,582,411 B1 | 6/2003 | Carstens et al. |
| 6,590,136 B1 | 7/2003 | Young et al. |
| 6,603,054 B2 | 8/2003 | Chen et al. |
| 6,642,430 B1 | 11/2003 | Busam et al. |
| 6,657,101 B1 | 12/2003 | Malmgren et al. |
| 6,664,439 B1 | 12/2003 | Arndt et al. |
| 6,673,057 B1 | 1/2004 | Ehrnsperger et al. |
| 6,673,981 B1 | 1/2004 | Stroembom et al. |
| 6,706,775 B2 | 3/2004 | Hermann et al. |
| 6,713,661 B1 | 3/2004 | Arndt et al. |
| 6,720,471 B1 | 4/2004 | Arndt et al. |
| 6,800,666 B2 | 10/2004 | Hahnle et al. |
| 6,811,842 B1 | 11/2004 | Ehrnsperger et al. |
| 6,943,200 B1 | 9/2005 | Corrand et al. |
| 6,989,005 B1 * | 1/2006 | LaVon .............. A61F 13/51498 604/385.14 |
| 7,056,404 B2 | 6/2006 | McFall et al. |
| 7,235,708 B2 | 6/2007 | Guidotti et al. |
| 7,285,576 B2 | 10/2007 | Hyde et al. |
| 7,462,756 B2 | 12/2008 | Malowaniec |
| 7,850,672 B2 | 12/2010 | Guidotti et al. |
| 8,207,393 B2 | 6/2012 | Bach |
| 8,426,670 B2 | 4/2013 | Nagasuna et al. |
| 8,707,717 B2 | 4/2014 | Fox et al. |
| 8,708,723 B2 | 4/2014 | Stoltz |
| 8,906,404 B2 | 12/2014 | Wellings |
| 2001/0041876 A1 | 11/2001 | Creagan et al. |
| 2001/0047456 A1 | 11/2001 | Schrobenhauzer et al. |
| 2003/0181884 A1 | 9/2003 | Carstens et al. |
| 2003/0191204 A1 | 10/2003 | Hermann et al. |
| 2003/0220039 A1 | 11/2003 | Chen et al. |
| 2004/0193129 A1 | 9/2004 | Guidotti et al. |
| 2005/0087292 A1 | 4/2005 | McFall et al. |
| 2005/0136224 A1 | 6/2005 | Nickel et al. |
| 2005/0250866 A1 | 11/2005 | Champ et al. |
| 2009/0270827 A1 | 10/2009 | Gundersen et al. |
| 2010/0162888 A1 | 7/2010 | Blucher et al. |
| 2012/0001122 A1 | 1/2012 | Wattebled |
| 2012/0108692 A1 | 5/2012 | Dyer |
| 2012/0237606 A1 | 9/2012 | Wellings |
| 2014/0050886 A1 | 2/2014 | Burgin et al. |
| 2014/0295134 A1 | 10/2014 | Wood et al. |
| 2014/0295135 A1 | 10/2014 | Thompson, Jr. et al. |
| 2015/0119837 A1 | 4/2015 | Thompson, Jr. et al. |
| 2015/0313770 A1 | 11/2015 | Hubbard, Jr. et al. |
| 2015/0335498 A1 | 11/2015 | Hubbard, Jr. et al. |

FOREIGN PATENT DOCUMENTS

| | | |
|---|---|---|
| EP | 0794751 | 11/1995 |
| EP | 1061966 | 3/1999 |
| EP | 1267769 | 1/2003 |
| EP | 1605881 | 1/2004 |
| EP | 1139951 | 10/2004 |
| EP | 1358894 | 11/2013 |
| GB | 1570485 | 7/1980 |
| GB | 2326828 | 1/1999 |
| WO | WO9611714 | 4/1996 |
| WO | WO9945878 | 9/1999 |
| WO | WO9947184 | 9/1999 |
| WO | WO9955269 | 11/1999 |
| WO | WO0000138 | 1/2000 |
| WO | WO0000136 | 12/2000 |
| WO | WO0059438 | 12/2000 |
| WO | WO0078369 | 12/2000 |
| WO | WO2001068022 | 9/2001 |
| WO | WO2003026707 | 10/2003 |
| WO | WO2004084784 | 10/2004 |
| WO | WO2004084785 | 10/2004 |

OTHER PUBLICATIONS

PCT International Search Report, PCT/US2015/029199, dated Jul. 21, 2015, 12 pages.

PCT International Search Report, PCT/US2015/032154, dated Aug. 26, 2015, 10 pages.

PCT International Search Report, PCT/US2016/060589, dated Feb. 3, 2017, 13 pages.

* cited by examiner

ABSORBENT STRUCTURE

FIELD OF THE INVENTION

The present invention relates to absorbent structures useful in absorbent articles such as diapers, incontinent briefs, training pants, diaper holders and liners, sanitary hygiene garments, and the like. Specifically, the present invention relates to an absorbent structure that have a smooth transition zone within the absorbent structure and a fibrous network.

BACKGROUND OF THE INVENTION

Many types of materials have been used in absorbent cores for absorbent articles including but not limited to cellulose, superabsorbent particles, foams, and fibrous substrates. Different stratum having potentially more than one layer are often combined to create an absorbent core. For example, a stratum may be designed for better acquisition while another stratum may be designed for storage. The two stratum are then combined by placing one in contact with the other to create an absorbent core.

Ultimately, in regards to an absorbent core, an acquisition layer is placed onto a storage layer to create the absorbent core. This may occur within a single stratum or using multiple stratum. This occurs with all the different core materials contemplated including the placement of one emulsion onto another emulsion prior to polymerization. When the layers or stratum are placed in contact, there is an understanding that fluid will eventually travel to the desired storage portion of the core. However, the interface between the acquisition and storage sections is neither designed nor optimized.

Within an absorbent core, the material structure is ultimately responsible for both driving force (capillary suction) and resistance to flow (inverse of through-plane permeability) in such a way that whenever the structure presents high surface/volume ratios the capillary suction increases (because more surfaces are available to sustain capillary forces) but the permeability decreases, because the flow becomes more tortuous. Conversely, whenever the ratio surface to volume is low in a porous material, then the resistance to flow is reduced (high permeability) at the expenses of the capillary suction.

Regardless of the actual nature of the capillary pressure curves for each individual layer comprising an absorbent structure used as diaper or hygienic pad, both industrial experience and flow through porous media theory show that the interface between the individual layer represents a significant barrier to fluid movement. This has to do with the presence of a discontinuity in the path of the moving fluid which does not 'like to jump' across layers. This ultimately results in residual moisture in the proximity of the surface/body interface which would negatively impact the consumer dryness feeling and perception.

Therefore there exists a need to create an absorbent core comprising a single stratum wherein the transition from acquisition to storage is optimized to increase the overall absorbent core efficiency. Additionally, there exists a need to characterize the transition. Lastly, there exists a need to integrate an absorbent core with an optimized acquisition to storage stratum into an absorbent article where the absorbent core is optimized to work with the topsheet so that the consumer has an improved experience.

SUMMARY OF THE INVENTION

An absorbent product comprising a topsheet, a backsheet, and an absorbent core is disclosed. The absorbent core comprising an absorbent structure comprising one or more stratum comprising one or more enrobeable elements, wherein a smooth transition zone is exhibited between an acquisition portion of the absorbent structure and a storage portion of the absorbent structure.

An absorbent product comprising a topsheet, a backsheet, and an absorbent core is further disclosed. The absorbent core comprising an absorbent structure comprising one or more stratum comprising one or more enrobeable elements and open cell foam, wherein a smooth transition zone is exhibited between an acquisition portion of the absorbent structure and a storage portion of the absorbent structure, wherein the smooth transition zone is demonstrated by a negative slope by a NMR technique.

An absorbent product comprising a topsheet, a backsheet, and an absorbent core is further disclosed. The absorbent core comprising an absorbent structure comprising one or more stratum comprising one or more enrobeable elements and open cell foam, wherein a smooth transition zone is exhibited between an acquisition portion of the absorbent structure and a storage portion of the absorbent structure, wherein the smooth transition zone is demonstrated by a negative slope by a NMR technique, wherein the smooth transition zone comprises of pores of average diameter between 20 micron and 60 micron.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
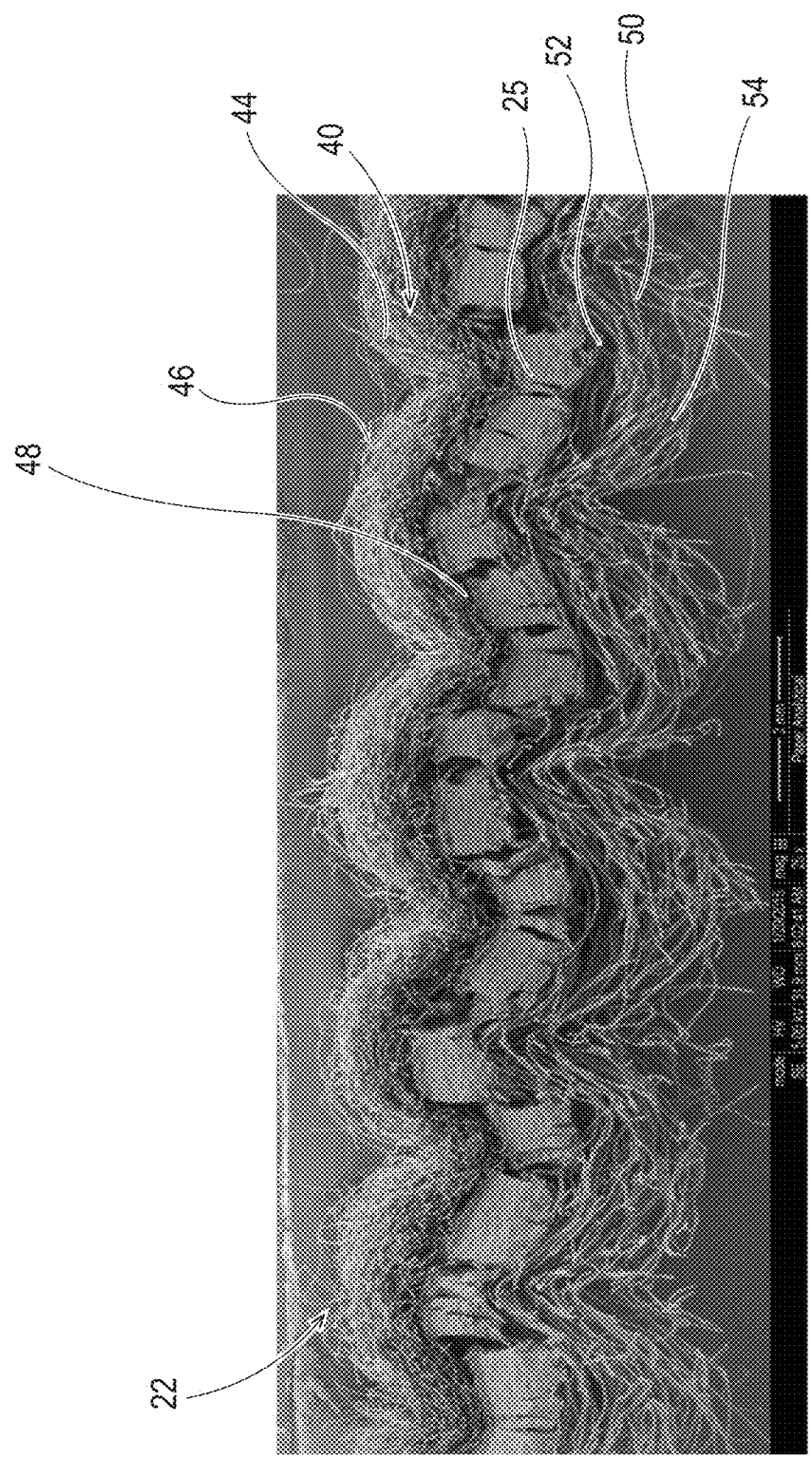
FIG. 1 is an SEM micrograph of a heterogeneous mass.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

In the following description the term "cellulose fibers" is used. Cellulose fibers comprise naturally occurring fibers based on cellulose, such as, for example cotton, linen, etc. Wood pulp fibers are one example of cellulose fibers according to the present invention. Man-made fibers derived from cellulose, such as regenerated cellulose, e.g. viscose or partially or fully acetylated cellulose derivatives (e.g. cellulose acetate or triacetate), are also considered as cellulose fibers according to the present invention.

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin, a panty liner, an adult incontinence product, a diaper, or any other product designed to absorb a bodily exudate. The absorbent structure of the present invention will be herein described in the context of a typical absorbent article, such as, for example, a sanitary napkin. Typically, such articles may comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that may be part of a fibrous structure. Fibers may be natural or synthetic. Fibers may be absorbent or non-absorbent.

A "fibrous structure" as used herein, refers to materials which may be broken into one or more fibers. A fibrous structure can be absorbent or adsorbent. A fibrous structure may exhibit capillary action as well as porosity and permeability.

As used herein, the term "immobilize" refers to the reduction or the elimination of movement or motion.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, electro-spinning, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size may also be expressed in denier, which is a unit of weight per length of fiber. The basis weight of laminate webs suitable for use in an article of the present invention may range from about 10 gsm to about 100 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "recovery energy" relates to an indicator of how well an absorbent structure or absorbent product may retain or regain is original shape. More specifically, "recovery energy" is a measure of the amount of work the absorbent structure or the absorbent product will perform against the consumer's body and/or garment following compression. Without being bound by theory, the upper limit for recovery energy should be the compressive energy i.e. a fully recovered product when removed from the consumer's body/garment. Dry recovery energy for between 1 and 20 cycles should be less than 250% the dry compressive energy of a new product.

As used herein, a "smooth transition zone" (STZ) refers to a transition zone between a portion of an absorbent structure designed for acquisition and a portion of an absorbent structure designed for storage that exhibits a slope that is negative on a plot having the Position in microns on an X axis wherein the bottom of the substrate is plotted closest to the origin and top is plotted furthest away and wherein the NMR signal is on the Y axis when analyzed using the Kinetics and 1D Liquid Distribution by NMR-MOUSE test protocol, after the second of two 0.5 ml fluid insults over two 5 minute test periods. The inventors have determined that an ideal acquisition and storage stratum will have a ratio of fluid stored in the acquisition layer to fluid stored in the storage layer of the stratum of greater than 1.5 to 1, greater than 2 to 1, greater than 2.5 to 1, or greater than 3 to 1 after the first and second 0.5 ml gushes.

As used herein, an "integrated topsheet/secondary topsheet zone" refers to a transition zone between a fibrous topsheet and a fibrous secondary topsheet that exhibits a slope that is negative on a plot having the Position in microns on an X axis wherein the bottom of the substrate is plotted closest to the origin and top is plotted furthest away and wherein the NMR signal is on the Y axis when analyzed using the Kinetics and 1D Liquid Distribution by NMR-MOUSE test protocol, after the second of two 0.5 ml fluid insults over two 5 minute test periods. The inventors have determined that an ideal topsheet and absorbent structure combination will leave a ratio of fluid retained in the topsheet to fluid stored in the absorbent structure of less than 1 to 10, less than 1 to 15, less than 1 to 20, less than 1 to 25, or less than 1 to 30.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers combined to create a single stratum which may be combined with other stratum to form an absorbent core. As used herein, a "tuft" or chad relates to discrete integral extensions of the fibers of a nonwoven web. Each tuft may comprise a plurality of looped, aligned fibers extending outwardly from the surface of the web. Each tuft may comprise a plurality of non-looped fibers that extend outwardly from the surface of the web. Each tuft may comprise a plurality of fibers which are integral extensions of the fibers of two or more integrated nonwoven webs.

As used herein, a "usage cycle" relates to the duration of use of the absorbent structure as it transitions from a dry state to a saturated wet state.

While particular embodiments of the present invention have been illustrated and described, it would be obvious to those skilled in the art that various other changes and modifications may be made without departing from the spirit and scope of the invention.

GENERAL SUMMARY

The present invention relates to an absorbent structure that contains a stratum comprising a fibrous network having a smooth transition zone between acquisition portion and storage portion of the absorbent core. The smooth transition zone is demonstrated using LF-NMR (Low Field Nuclear Magnetic Resonance) as a methodology to characterize fluid partitioning inside complex porous media structure to show the existence of a smooth transition zone and to show the advantage created by the smooth transition zone. A single stratum may comprise one or more absorbent layers. One or more absorbent core stratums may be a heterogeneous mass comprising enrobeable elements and open cell foam, a cellulose layer, a layer comprising a substrate, a superabsorbent, and an adhesive layer, a layer comprising airfelt fibers, and a layer of foam.

A stratum may be a heterogeneous mass comprising one or more enrobeable elements and one or more discrete open cell foam pieces. The heterogeneous mass has a depth, a width, and a height. The absorbent structure may be used as any part of an absorbent article including, for example, a part of an absorbent core, as an absorbent core, and/or as a topsheet for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. The absorbent structure may be used in any product utilized to absorb and retain a fluid including surface wipes. The absorbent structure may be used as a paper towel. Exemplary absorbent articles in the context of the present invention are disposable absorbent articles.

The absorbent structure single stratum may comprise a heterogeneous mass layer as those described in U.S. patent application No. 61/988,565, filed May 5, 2014; U.S. patent application No. 62/115,921, filed Feb. 13, 2015; or U.S. patent application No. 62/018,212. The heterogeneous mass layer has a depth, a width, and a height.

The absorbent structures single stratum may be a heterogeneous mass comprising enrobeable elements and one or more portions of foam pieces. The discrete portions of foam pieces are open-celled foam. The foam may be a High Internal Phase Emulsion (HIPE) foam.

The absorbent structure single stratum may be an absorbent core for an absorbent article wherein the absorbent core comprises a heterogeneous mass comprising fibers and one or more discrete portions of foam that are immobilized in the heterogeneous mass or may be combined with other layers to form an absorbent core.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The present invention relates to an absorbent structure single stratum that contains one or more discrete open-cell foam pieces foams that are integrated into a heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass may have void space found between the enrobeable elements, between the enrobeable elements and the enrobed elements, and between enrobed elements. The void space may contain a gas such as air. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the, such as for example, between 20 g/g and 190 g/g of the heterogeneous mass, such as, for example 30 g/g, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

A discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

A discrete open-cell foam piece may be immobilized such that the discrete open-cell foam piece does not change location within the heterogeneous mass during use of the absorbent structure.

A plurality of discrete open-cell foams may be immobilized such that the discrete open-cell foam pieces do not change location within the heterogeneous mass during use of the absorbent structure.

One or more discrete foam pieces may be immobilized within the heterogeneous mass such that the one or more discrete foam pieces do not change location after being spun at 300 rotations per minute for 30 seconds.

The open-cell foam pieces may be discrete. Open-cell foam pieces are considered discrete in that they are not continuous throughout the entire heterogeneous mass. Not continuous throughout the entire heterogeneous mass represents that at any given point in the heterogeneous mass, the open-cell absorbent foam is not continuous in at least one of the cross sections of a longitudinal, a vertical, and a lateral plane of the heterogeneous mass. The absorbent foam may or may not be continuous in the lateral and the vertical planes of the cross section for a given point in the heterogeneous mass. The absorbent foam may or may not be continuous in the longitudinal and the vertical planes of the cross section for a given point in the heterogeneous mass. The absorbent foam may or may not be continuous in the longitudinal and the lateral planes of the cross section for a given point in the heterogeneous mass.

When the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. A foam piece may be surrounded by the elements that make up the enrobeable elements. A foam piece may be located on the outer perimeter of the heterogeneous mass such that only a portion of the foam piece is entangled with the elements of the heterogeneous mass.

The open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. The open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces. The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

Dependent upon the desired foam density, polymer composition, specific surface area, or pore-size (also referred to as cell size), the open-celled foam may be made with different chemical composition, physical properties, or both. For instance, dependent upon the chemical composition, an open-celled foam may have a density of 0.0010 g/cc to about 0.25 g/cc, or from 0.002 g/cc to about 0.2 g/cc, or from about 0.005 g/cc to about 0.15 g/cc, or from about 0.01 g/cc to about 0.1 g/cc, or from about 0.02 g/cc to about 0.08 g/cc, or about 0.04 g/cc.

Open-cell foam pore-sizes may range in average diameter of from 1 to 800 such as, for example, between 50 and 700 between 100 and 600 between 200 and 500 between 300 and 400 μm.

The foam pieces may have a relatively uniform cell size. For example, the average cell size on one major surface may be about the same or vary by no greater than 10% as compared to the opposing major surface. The average cell size of one major surface of the foam may differ from the opposing surface. For example, in the foaming of a thermosetting material it is not uncommon for a portion of the cells at the bottom of the cell structure to collapse resulting in a lower average cell size on one surface. The cell size may be determined based upon the method found below.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 μm in average diameter size are in fluid communication with at least one adjoining cell.

In addition to being open-celled, the foams may be sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

For example when used in certain absorbent articles, an open-cell foam may be flexible and exhibit an appropriate glass transition temperature (Tg). The Tg represents the midpoint of the transition between the glassy and rubbery states of the polymer.

The Tg of a region may be less than about 200° C. for foams used at about ambient temperature conditions, or less than about 90° C. The Tg may be less than 50° C.

The open-cell foam pieces may be distributed in any suitable manner throughout the heterogeneous mass. The open-cell foam pieces may be profiled along the vertical axis such that smaller pieces are located above larger pieces. Alternatively, the pieces may be profiled such that smaller pieces are below larger pieces. The open-cell pieces may be profiled along a vertical axis such that they alternate in size along the axis.

The open-cell foam pieces may be profiled along the longitudinal axis such that smaller pieces are located in front of larger pieces. Alternatively, the pieces may be profiled such that smaller pieces are behind larger pieces. The open-cell pieces may be profiled along a longitudinal axis such that they alternate in size along the axis.

The open-cell foam pieces may be profiled along the lateral axis such the size of the pieces goes from small to large or from large to small along the lateral axis. Alternatively, the open-cell pieces may be profiled along a lateral axis such that they alternate in size along the axis.

The open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

The open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. The open-cell foam pieces may be distributed in a manner that forms a design or shape when viewed from a top planar view. The open-cell foam pieces may be distributed in a manner that forms stripes, ellipticals, squares, or any other known shape or pattern.

The distribution may be optimized dependent on the intended use of the heterogeneous mass. For example, a different distribution may be chosen for the absorption of aqueous fluids such as urine when used in a diaper or water when used in a paper towel versus for the absorption of a proteinaceous fluid such as menses. Further, the distribution may be optimized for uses such as dosing an active or to use the foam as a reinforcing element.

Different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The foam pieces may be similar in composition yet exhibit different properties. For example, using HIPE foam, some foam pieces may be thin until wet while others may have been expanded within the heterogeneous mass.

The foam pieces and enrobeable elements may be selected to complement each other. For example, a foam that exhibits high permeability with low capillarity may enrobe an element that exhibits high capillarity to wick the fluid through the heterogeneous mass. It is understood that other combinations may be possible wherein the foam pieces complement each other or wherein the foam pieces and enrobeable elements both exhibit similar properties.

Profiling may occur using more than one heterogeneous mass with each heterogeneous mass having one or more types of foam pieces. The plurality of heterogeneous masses may be layered so that the foam is profiled along any one of the longitudinal, lateral, or vertical axis based on one or more characteristics of the open-cell foam pieces for an overall product that contains the plurality of heterogeneous masses. Further, each heterogeneous mass may have a different enrobeable element to which the foam is attached. For example, a first heterogeneous mass may have foam particles enrobing a nonwoven while a second heterogeneous mass adjacent the first heterogeneous mass may have foam particles enrobing a film or one surface of a film.

The open-celled foam may be a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. The aqueous phase to oil phase ratio may be between about 10:1 and about 75:1, and the aqueous phase to oil phase ratio may be between about 13:1 and about 65:1. This is termed the "water-to-oil" or W:O ratio and may be used to determine the density of the resulting polyHIPE foam. As discussed, the oil phase may contain one or more of monomers, comonomers, photoinitiators, crosslinkers, and emulsifiers, as well as optional components. The water phase may contain water and one or more components such as electrolyte, initiator, or optional components.

The open-cell foam may be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, or after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE may then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion may be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. Foam pieces may be squeezed free of most of the aqueous phase by using compression, for example by running the heterogeneous mass comprising the foam pieces through one or more pairs of nip rollers. The nip rollers may be positioned such that they squeeze the aqueous phase out of the foam pieces. The nip rollers may be porous and have a vacuum applied from the inside such that they assist in drawing aqueous phase out of the foam pieces. Nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller may be pressurized while the other, for example the second nip roller, may be evacuated, so as to both blow and draw the aqueous phase out the of the foam. The nip rollers may also be heated to assist in removing the aqueous phase. Nip rollers may be applied to non-rigid foams, that is, foams whose walls would not be destroyed by compressing the foam pieces.

In place of or in combination with nip rollers, the aqueous phase may be removed by sending the foam pieces through a drying zone where it is heated, exposed to a vacuum, or a combination of heat and vacuum exposure. Heat may be applied, for example, by running the foam though a forced air oven, IR oven, microwave oven or radiowave oven. The extent to which a foam is dried depends on the application. Greater than 50% of the aqueous phase may be removed. Greater than 90%, and in still other embodiments greater than 95% of the aqueous phase may be removed during the drying process.

Open-cell foam may be produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. "Toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. Coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. Ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio)phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo[2-hydroxy-2-methyl-1-[4-(1-methylvinyl)phenyl]propanone] (sold by Lambeth spa, Gallarate, Italy as ESACURE® KIP EM.

The dispersed aqueous phase of a HIPE may have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte may include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator may be present at up to about 20 mole percent based on the total moles of polymerizable monomers present in the oil phase. The initiator may be present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. To reduce the potential for premature polymerization which may clog the emulsification system, addition of the initiator to the monomer phase may be just after or near the end of emulsification.

Photoinitiators present in the aqueous phase may be at least partially water soluble and may have between about 0.05% and about 10%, and in certain embodiments between about 0.2% and about 10% by weight of the aqueous phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzal acetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that may be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web such as, for example, nonwoven, a fibrous structure, an airlaid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. The enrobeable elements may be treated to be made hydrophobic. The enrobeable elements may be treated to become hydrophilic.

The constituent fibers of the heterogeneous mass may be comprised of polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a super absorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers may range from about 0.1 denier to about 100 denier.

In one aspect, known absorbent web materials in an as-made may be considered as being homogeneous throughout. Being homogeneous, the fluid handling properties of the absorbent web material are not location dependent, but are substantially uniform at any area of the web. Homogeneity may be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability may be accomplished without a decrease in capillarity.

The heterogeneous mass may also include superabsorbent material that imbibe fluids and form hydrogels. These materials are typically capable of absorbing large quantities of body fluids and retaining them under moderate pressures. The heterogeneous mass may include such materials dispersed in a suitable carrier such as cellulose fibers in the form of fluff or stiffened fibers.

The heterogeneous mass may include thermoplastic particulates or fibers. The materials, and in particular thermoplastic fibers, may be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g. per sq. of centimeter of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e. unbent) or crimped (i.e. bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties-of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The heterogeneous mass may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

However structured, the total absorbent capacity of the heterogeneous mass containing foam pieces should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins. The heterogeneous mass may also include other optional components sometimes used in absorbent webs. For example, a reinforcing scrim may be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; disposable diapers; incontinence articles, for example pads, adult diapers; home-care articles, for example wipes, pads, towels; and beauty care articles, for example pads, wipes, and skin care articles, such as used for pore cleaning.

The heterogeneous mass may be used as an absorbent core for an absorbent article. The absorbent core may be relatively thin, less than about 5 mm in thickness, or less than about 3 mm, or less than about 1 mm in thickness. Cores having a thickness of greater than 5 mm are also contemplated herein. Thickness may be determined by measuring the thickness at the midpoint along the longitudinal centerline of the absorbent structure by any means known in the art for doing while under a uniform pressure of 0.25 psi. The absorbent core may comprise absorbent gelling materials (AGM), including AGM fibers, as is known in the art.

The heterogeneous mass may be formed or cut to a shape, the outer edges of which define a periphery. Additionally, the heterogeneous mass may be continuous such that it may be rolled or wound upon itself, with or without the inclusion of preformed cut lines demarcating the heterogeneous mass into preformed sections.

When used as an absorbent core, the shape of the heterogeneous mass may be generally rectangular, circular, oval, elliptical, tapered at one or both ends, hourglass, star, horseshoe, hearts, the like, or combinations thereof. Absorbent core may be generally centered with respect to the longitudinal centerline and transverse centerline of an absorbent article. The profile of absorbent core may be such that more absorbent is disposed near the center of the absorbent article. For example, the absorbent core may be thicker in the middle, and tapered at the edges in a variety of ways known in the art.

The presence of a smooth transition zone provides continuity of capillary suction and of fluid path, which are essential to proper dewatering of the acquisition layer, re-establishing the suction needed for further acquiring fluid from the topsheet layer.

Further, Applicants have found that by using a fibrous structure in the acquisition portion of the absorbent structure intimately connected to the topsheet on one surface of the acquisition portion of the stratum and intimately connected to the storage portion of the absorbent structure on the other surface of the acquisition portion of the stratum allows for faster fluid acquisition, leading to improved topsheet dryness after consecutive 0.5 ml gushes. For example, the absorbent stratum, as shown in FIG. 3, exhibits a topsheet residual moisture after the second 0.5 ml gush of approximately 0.03 a.u. after 5 minutes, while in FIG. 2, the structure exhibits a topsheet a.u. after the second 0.5 ml gush of approximately 0.15 a.u after five minutes. As shown in FIG. 3, the absorbent structure may exhibit a topsheet residual moisture after a second 0.5 ml gush of approximately between 0.1 a.u. and 0.01 a.u., such as, for example, 0.09 a.u., 0.08 a.u., 0.07 a.u., 0.06 a.u., 0.05 a.u., 0.04 a.u., and 0.03 a.u. after 5 minutes.

This has been achieve through the creation of a heterogeneous mass absorbent composite structure comprising an acquisition layer comprised of enrobeable elements with very high permeability (nonwoven substrate), a storage layer with very high capillary suction (a high internal phase emulsion), and a transition zone exhibited by the area where the enrobeable elements are fully enrobed by the high internal phase emulsion foam.

The capillary suction is driven mostly by the high internal phase emulsion foam layer with a progressive decrease in capillary suction (bigger cells) as we move towards the top. The intrinsic properties of the foam (average cell size and cell size distribution, average window size and window size distribution, porosity, caliper and surface treatment) are then gradually transitioned to the intrinsic properties of the substrate/acquisition layer through the presence of a transition layer where the two are intimately intertwined.

Without being bound by theory, it is believed that this construction significantly improves the fluid handling performance of the system vs. having the substrate glued on top of a single layer of HIPE foam by mean of two effects: 1) it increases the speed of acquisition of the absorbent structure by providing a capillary gradient the fluid would preferentially follow and 2) it provides a better mean for dewatering the Topsheet, and restoring the pre-gush saturation level in the nonwoven material thanks to the fluid path continuity (i.e. the absence of a discontinuity—aka, void—in the construction).

Specifically, without being bound by theory, it has been found that a smooth transition zone Demonstrating the superiority of such a construction requires a very specific methodology capable of showing fluid partitioning within an absorbent article and how far/close the fluid is to the surface/consumer skin. This is covered in the section below disclosing the NMR test method and the data shown in FIGS. 2 and 3.

The absorbent structure heterogeneous mass may serve as any portion of an absorbent article. The absorbent structure heterogenous mass may serve as the absorbent core of an absorbent article. A stratum may serve as a portion of the absorbent core of an absorbent article. More than one absorbent structure stratum may be combined wherein each absorbent structure single stratum differs from at least one other absorbent structure single stratum. The different two or more absorbent structures stratums may be combined to form an absorbent core. The absorbent article may further comprise a topsheet and a backsheet.

The absorbent structure single stratum may be used as a topsheet for an absorbent article. The absorbent structure single stratum may be combined with an absorbent core or may only be combined with a backsheet.

The absorbent structure single stratum may be combined with any other type of absorbent layer such as, for example, a storage or acquisition layer comprising a layer of cellulose, a layer comprising superabsorbent gelling materials, a layer of absorbent airlaid fibers, or a layer of absorbent foam. Other absorbent layers not listed are contemplated herein.

The absorbent structure single stratum may be utilized by itself for the absorption of fluids without placing it into an absorbent article.

An absorbent article may comprise a liquid pervious topsheet. The topsheet suitable for use herein may comprise wovens, non-wovens, and/or three-dimensional webs of a liquid impermeable polymeric film comprising liquid permeable apertures. The topsheet for use herein may be a single layer or may have a multiplicity of layers. For example, the wearer-facing and contacting surface may be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

The absorbent articles of the absorbent structure may also comprise a backsheet and a topsheet. The backsheet may be used to prevent the fluids absorbed and contained in the absorbent structure from wetting materials that contact the absorbent article such as underpants, pants, pajamas, undergarments, and shirts or jackets, thereby acting as a barrier to fluid transport. The backsheet may also allow the transfer of at least water vapour, or both water vapour and air through it.

Especially when the absorbent article finds utility as a sanitary napkin or panty liner, the absorbent article may be also provided with a panty fastening means, which provides means to attach the article to an undergarment, for example a panty fastening adhesive on the garment facing surface of the backsheet. Wings or side flaps meant to fold around the crotch edge of an undergarment may be also provided on the side edges of the napkin.

FIG. 1 is an SEM micrograph of a heterogeneous mass 22 after formation means or the forming of canals. As shown in FIG. 1, the absorbent stratum 40 is a heterogeneous mass 22 comprising a first planar nonwoven 44 having a first surface 46 and a second surface 48 and a second planar nonwoven 50 having a first surface 52 and a second surface 54. An open cell foam piece 25 enrobes a portion of the first planar nonwoven 44 and a portion of the second planar nonwoven 50. The planar nowovens are shown as wavy due to the impact of the formation means.

As shown in FIG. 1, the enrobeable elements are highly porous and designed to work as an acquisition layer for the absorbent core while the non-integrated foam serves as a storage layer. This allows creating capillary suction continuity and a capillary suction gradient from top to bottom, which would drive the fluid into the storage core layer (HIPE foam as shown).

Figure 2:
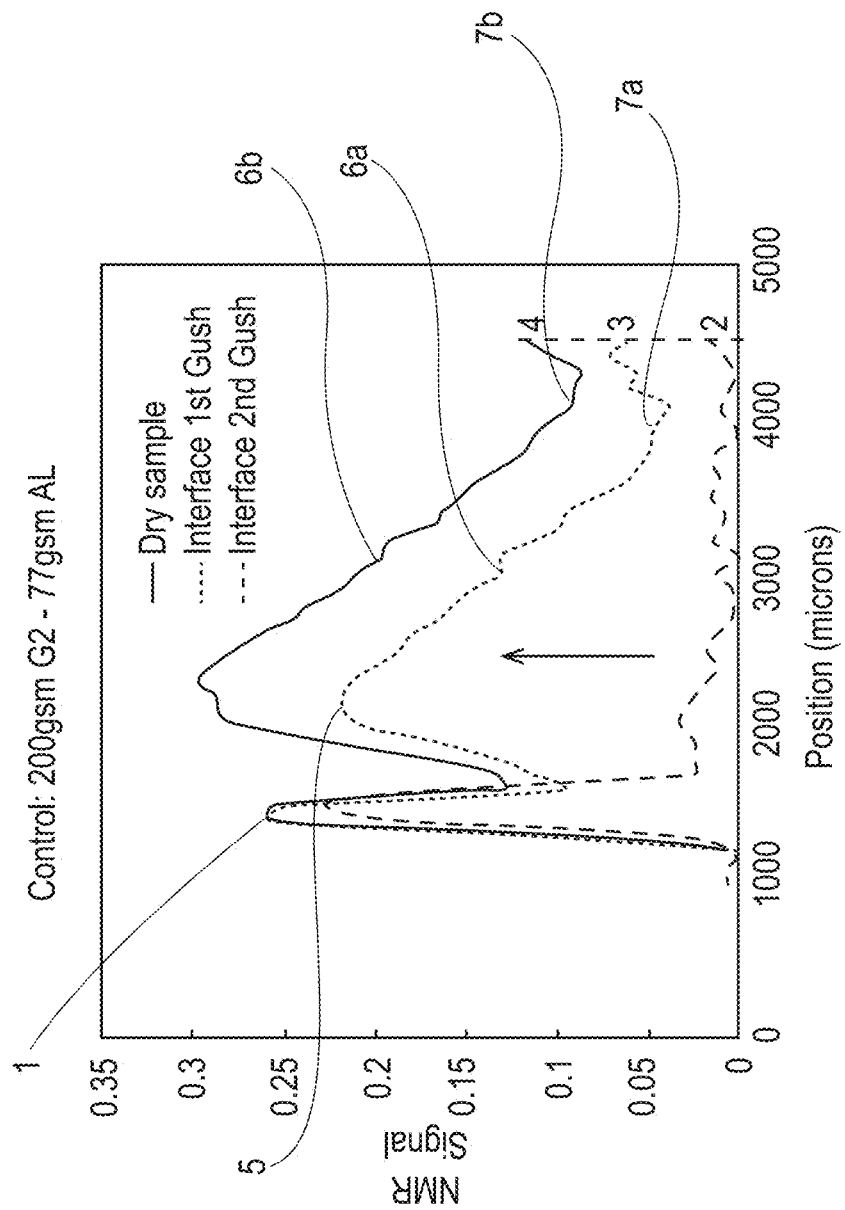
FIG. 2 shows a plot of an NMR profile.
Figure 3:
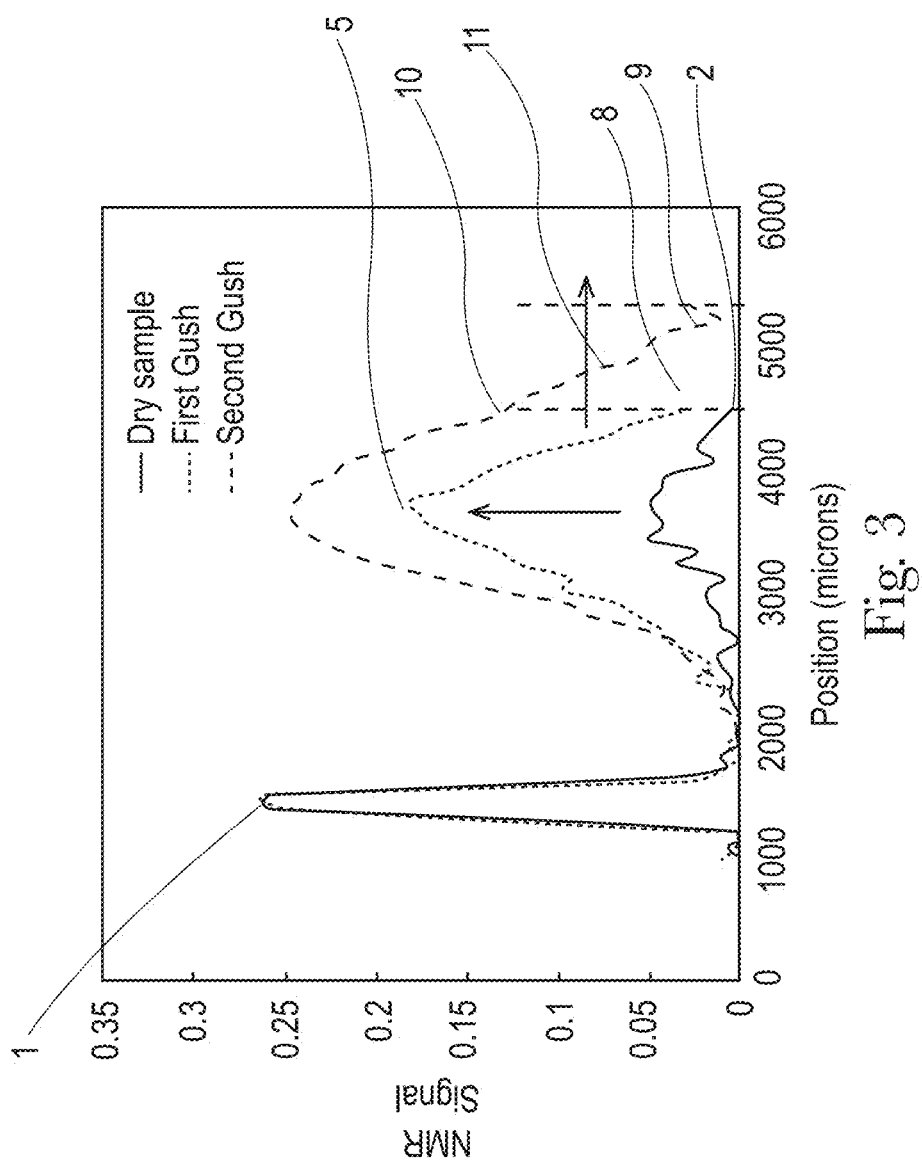
FIG. 3 shows a plot of an NMR profile.

FIGS. 2 and 3 show two plots of NMR profiles of signal (which correlates linearly with moisture content) as function of position within product respectively for a current marketed product (FIG. 2) and the absorbent core of FIG. 1 (FIG. 3) using the same topsheet as the marketed product.

As shown in FIGS. 2 and 3, as viewed from left to right, the first (1) peak, consistent across the three samples is the double-side tape placed to identify the beginning of a specimen. Starting with the current market product in FIG. 2, we see a scan of the dry sample (2), then a scan of the sample after the first 0.5 mL gush (3) and then a scan of the sample after the second 0.5 mL gush (4). Each scan is taken 5 min after gush.

As shown in FIG. 2, the first peak (5) in the scan is the fluid distribution of the first 0.5 ml gush across the gradient core/acquisition structure. There is a linear trend going from the absorbent core (CORE) down the Secondary topsheet (STS) and Topsheet (TS) which reflect the capillary suction gradient (i.e. at equilibrium, the partitioning of fluid follows capillary potentials, hence more fluid is stored by higher capillary suction elements). Within the curve, we can identify that the majority of the first 0.5 ml gush has entered the absorbent core, that the interface (6a) between the absorbent core and the secondary top sheet (gap) can be identified by the peak-valley transition, and that another transition (7a) can be seen from Topsheet to the secondary topsheet. Within the curve, we can identify that the majority of the second 0.5 ml gush has also entered the absorbent core, that the interface (6b) between the absorbent core and the secondary top sheet (gap) can be identified by the peak-valley transition, and that another transition (7b) can be seen from Topsheet to the secondary topsheet. The topsheet remains wet after the second gush (close to 0.15 a.u., or center of STS after first gush). As shown in FIG. 2, in the positional range (4200 to 4500 microns) consistent with the TS, one can see an increase in the slope or an inflection indicating an increase in fluid on the topsheet between the acquisition scan of the first gush and the acquisition scan of the second gush. As shown in FIG. 2, the interface between any two layers is characterized by an inflection point in the acquisition scan wherein the slope is greater than or equal to zero. These inflection points are identified by 6a, 6b, 7a, and 7b.

Finally, viewing FIG. 3, one can see how the absorbent structure of FIG. 1 shows a smooth transition zone. Specifically, as seen in FIG. 3, one can see in scan (8) that the vast majority of the first 0.5 ml gush has entered the absorbent core, and very little fluid is left on either the STS or the TS (not shown). The third scan (9) of FIG. 3 represents the second 0.5 ml gush. As shown by the third scan (9), the second 0.5 ml gush has also entered the absorbent core and the interfaces between the acquisition portion and the storage portion (10) of the stratum and between the acquisition portion and the topsheet (11) both exhibit smooth transition zones with slopes less than zero. As shown in FIG. 3, after the second 0.5 ml gush, the topsheet exhibits an a.u. of less than 0.03. For reference, the absorbent stratum analyzed in FIG. 3 is a 27:1 oil to water ratio HIPE extruded onto Fitesa 60 gsm AQL and then polymerized. Once polymerized 30 gsm Spunlace is glued on the other side. The core is Ring-Rolled (mechanically opened) to about 30% width extension.

EXAMPLES

A. An absorbent product comprising a topsheet, a backsheet, and an absorbent core, the absorbent core comprising an absorbent structure comprising one or more stratum comprising one or more enrobeable elements, wherein a smooth transition zone is exhibited between an acquisition portion of the absorbent structure and a storage portion of the absorbent structure.

B. The absorbent product according to paragraph A, wherein the enrobeable elements comprise of nonwoven fibers having an average thickness, as measured per SEM, ca. between 100 and 600 um.

C. The absorbent product according to paragraph A or B, wherein the smooth transition zone comprises open-cell foam comprising pores having an average diameter between 20 micron and 60 micron.

D. The absorbent according to paragraph C, wherein the smooth transition zone comprises pores having an average diameter between 30 micron and 40 micron.

E. The absorbent product according to any of paragraphs A-D, wherein the smooth transition zone to caliper ratio is between 0.1 and 0.4.

F. The absorbent product according to any of paragraphs A-E, wherein the ratio of the Capillary Work Potential of the topsheet to the Capillary Work Potential to the absorbent structure is below 1.4.

G. The absorbent product according to paragraph C, wherein the ratio of the basis weight of the fibers to the basis weight of the open-cell foam is below 0.48.

H. The absorbent product according to paragraph C, wherein the open-cell foam comprises an average cell size above 20 micron and a basis weight above 110 gsm.

I. An absorbent product comprising a topsheet, a backsheet, and an absorbent core, the absorbent core comprising an absorbent structure comprising one or more stratum comprising one or more enrobeable elements and open cell foam, wherein a smooth transition zone is exhibited between an acquisition portion of the absorbent structure and a storage portion of the absorbent structure, wherein the smooth transition zone is demonstrated by a negative slope by a NMR technique.

J. The absorbent product according to paragraph I, wherein the enrobeable elements comprise of nonwoven fibers having an average thickness, as measured per SEM, ca. between 100 and 600 um.

K. The absorbent product according to paragraph I or J, wherein the smooth transition zone comprises pores having an average diameter between 20 micron and 60 micron.

L. The absorbent product according to any of paragraphs I-K, wherein the smooth transition zone comprises pores having an average diameter between 30 micron and 40 micron.

M. The absorbent product according to any of paragraphs I-L, wherein the smooth transition zone to caliper ratio is between 0.1 and 0.4.

N. The absorbent product according to any of paragraphs I-M, wherein the ratio of the Capillary Work Potential of the topsheet to the Capillary Work Potential to the carrier is below 1.4.

O. The absorbent product according to any of paragraphs I-N, wherein the ratio of the basis weight of the carrier to the basis weight of the foam is below 0.48.

P. The absorbent product according to any of paragraphs I-O, wherein the open-cell foam comprises an average cell size above 20 micron and a basis weight above 110 gsm.

Q. An absorbent product comprising a topsheet, a backsheet, and an absorbent core, the absorbent core comprising an absorbent structure comprising one or more stratum comprising one or more enrobeable elements and open cell foam, wherein a smooth transition zone is exhibited between an acquisition portion of the absorbent structure and a storage portion of the absorbent structure, wherein the smooth transition zone is demonstrated by a negative slope by a NMR technique, wherein the smooth transition zone comprises of pores of average diameter between 20 micron and 60 micron.

R. The absorbent product according to paragraph Q, wherein the smooth transition zone comprises pores having an average diameter between 30 micron and 40 micron.

S. The absorbent product according to paragraph Q or R, wherein the smooth transition zone to caliper ratio is between 0.1 and 0.4.

Kinetics and 1D Liquid Distribution by NMR-MOUSE

Figure 6:
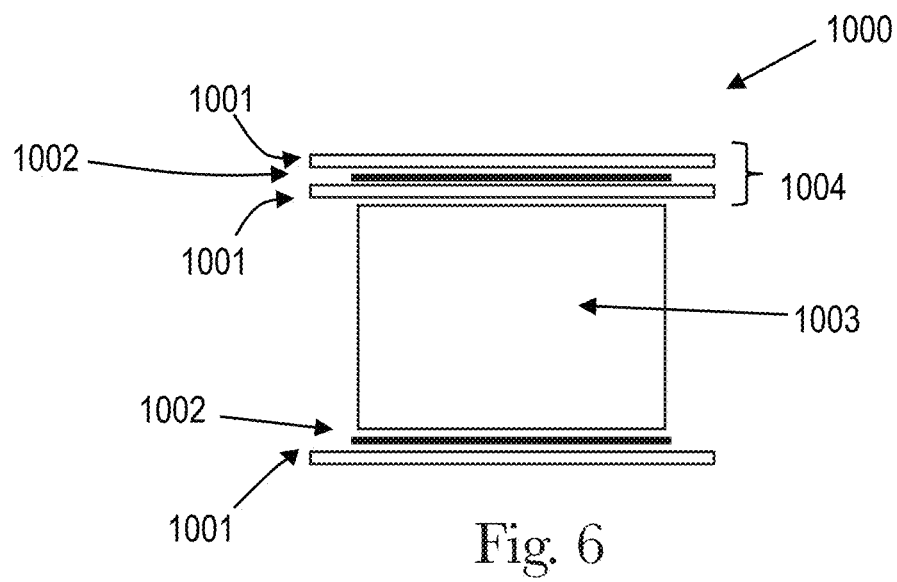
FIG. 6 shows a portion of a NMR sensor.
Figure 7:
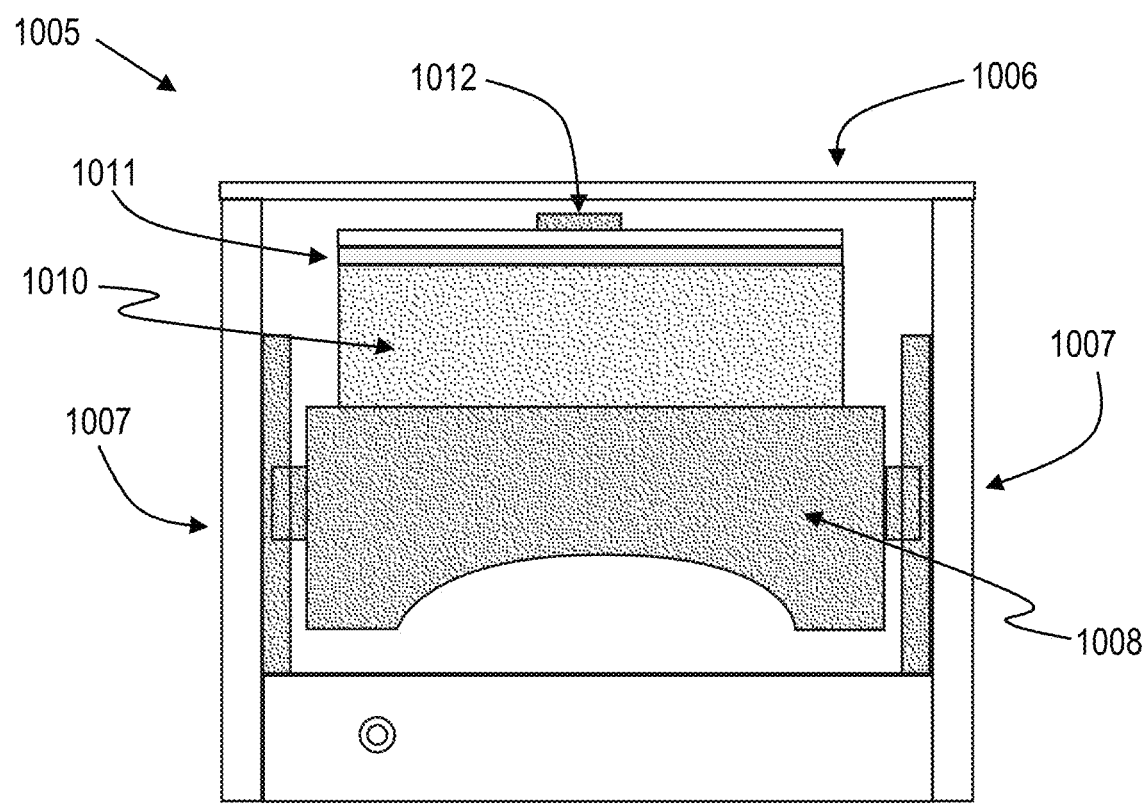
FIG. 7 shows a portion of a NMR sensor.

The NMR-MOUSE (Mobile Universal Surface Explorer) is a portable open NMR sensor equipped with a permanent magnet geometry that generates a highly uniform gradient perpendicular to the scanner surface (shown in FIGS. 6-7). A frame 1007 with horizontal plane 1006 supports the specimen and remains stationary during the test. A flat sensitive volume of the specimen is excited and detected by a surface rf coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution.

An exemplary instrument is the Profile NMR-MOUSE model PM25 with High-Precision Lift available from Magritek Inc., San Diego, Calif. Requirements for the NMR-MOUSE are a 100 µm resolution in the z-direction, a measuring frequency of 13.5 MHz, a maximum measuring depth of 25 mm, a static gradient of 8 T/m, and a sensitive volume (x-y dimension) of 40 by 40 mm$^2$. Before the instrument can be used, perform phasing adjustment, check resonance frequency and check external noise level as per the manufacturer's instruction. A syringe pump capable of delivering test fluid in the range of 1 mL/min to 5 mL/min±0.01 mL/min is used to dose the specimen. All measurements are conducted in a room controlled at 23° C.±0.5° C. and 50%±2% relative humidity.

Two test solutions are prepared. The first is 0.9% w/v saline solution prepared as 9.0 g of NaCl diluted to 1 L deionized water. The second is Paper Industry Fluid (PIF) prepared as 15 g carboxymethylcellulose, 10 g NaCl, 4 g $NaHCO_3$, 80 g glycerol (all available from SigmaAldrich) in 1000 g distilled water. 2 mM/L of Diethylenetriaminepentaacetic acid gadolinium (III) dihydrogen salt (available from SigmaAldrich) is added to each. After addition the solutions are stirred using an shaker at 160 rpm for one hour. Afterwards the solutions are checked to assure no visible undissolved crystals remain. The solution is prepared 10 hours prior to use.

Products for testing are conditioned at 23° C.±0.5° C. and 50%±2% relative humidity for two hours prior to testing. Identify the intersection of the lateral and longitudinal center line of the product. Cut a 40.0 mm by 40.0 mm specimen from the product, centered at that intersection, with the cut edges parallel and perpendicular to the longitudinal axis of the product. The garment facing side of the specimen 1003 is mounted on a 50 mm×50 mm×0.30 mm glass slide 1001 using a 40.0 mm by 40.0 mm piece of double-sided tape 1002 (tape must be suitable to provide NMR Amplitude signal). A top cap 1004 is prepared by adhering two 50 mm×50 mm×0.30 mm glass slides 1001 together using a 40 mm by 40 mm piece of two-sided tape 1002. The cap is then placed on top of the specimen. The two tape layers are used as functional markers to define the dimension of the specimen by the instrument.

Figure 4A:
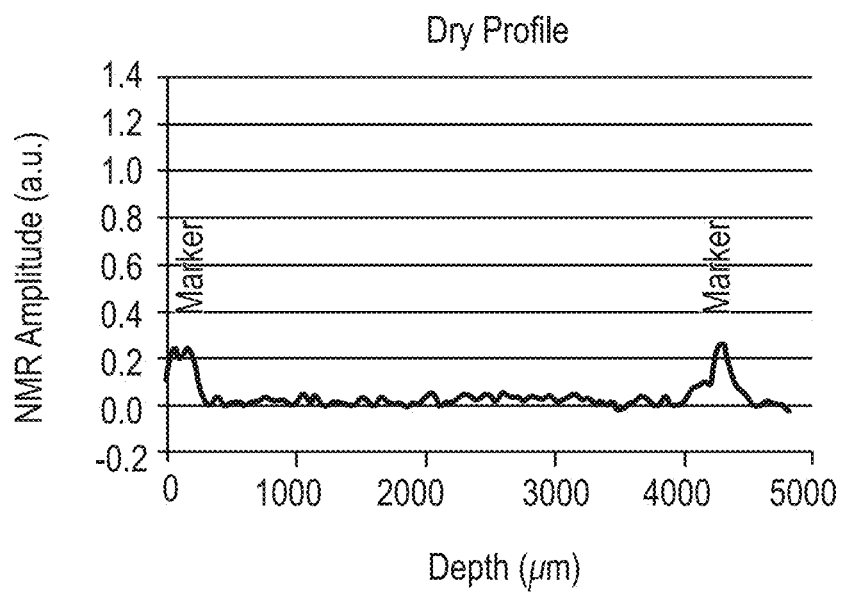
FIGS. 4A-B shows a plot of an NMR profile.

First a 1-D Dry Distribution Profile of the specimen is collected. Place the prepared specimen onto the instrument aligned over top the coils. Program the NMR-MOUSE for a Carr-Purcell-Meiboom-Gill (CPMG) pulse sequence consisting of a 90° x-pulse follow by a refocusing pulse of 180° y-pulse using the following conditions:

Repetition Time=500 ms
Number of Scans=8
Number of Echoes=8
Resolution=100 μm
Step Size=−100 μm Collect NMR Amplitude data (in arbitrary units, a.u.) versus depth (μm) as the high precision lift steps through the specimen's depth. A representative graph is shown in FIG. 4A.

The second measure is the Kinetic Experiment of the test fluid moving though the sensitive NMR volume as test fluid is slowly added to the top of the specimen. The "trickle" dose is followed by a "gush" dose added using a calibrated dispenser pipet. Program the NMR-MOUSE for a CPMG pulse sequence using the following conditions:

Measurement Depth=5 mm
Repetition Time=200 ms
90° Amplitude=−7 dB
180° Amplitude=0 dB
Pulse Length=5 μs Echo Time=90 μs
Number of Echoes=128
Echo Shift=1 μs
Experiments before trigger=50
Experiments after trigger=2000
Rx Gain=31 dB
Acquisition Time=8 μs
Number of Scans=1

Rx Phase is determined during the phase adjustment as described by the vendor. A value of 230° was typical for our experiments. Pulse length depends on measurement depth which here is 5 mm. If necessary the depth can be adjusted using the spacer 1011.

Figure 5:
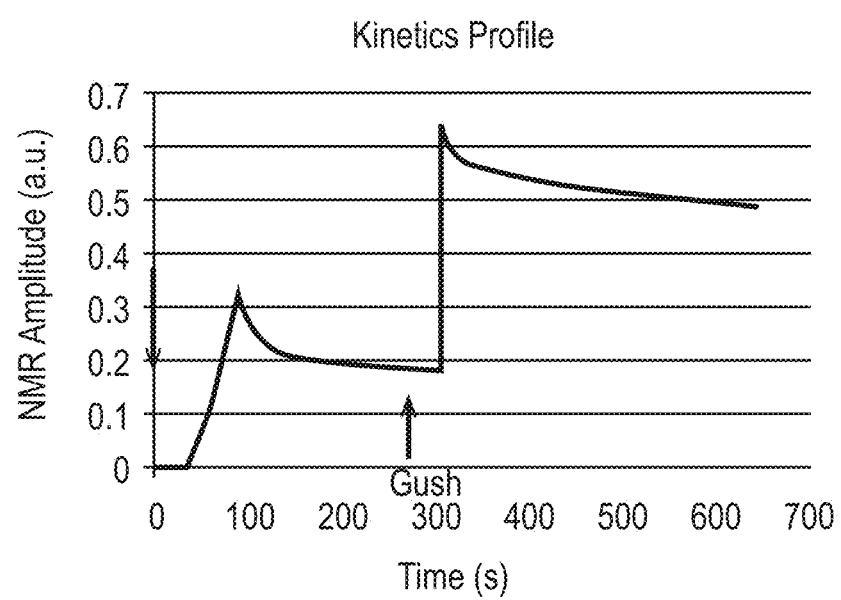
FIG. 5 shows a kinetic plot of an NMR profile.

Using the precision lift adjust the height of the specimen so that the desired target region is aligned with the instruments sensitive volume. Target regions can be chosen based on SEM cross sections. Program the syringe pump to deliver 1.00 mL/min±0.01 mL for 1.00 min for PIF test fluid or 5.00 mL/min±0.01 mL for 1.00 min for 0.9% Saline test fluid. Start the measurement and collect NMR Amplitude (a.u.) for 50 experiments before initiating fluid flow to provide a signal baseline. Position the outlet tube from the syringe pump over the center of the specimen and move during applying liquid over the total sample surface, but do not touch the borders of the sample. Trigger the system to continue collection of NMR amplitude data while simultaneously initiating fluid flow for 1 mL over 60 sec. At 300 sec after the trigger, add 0.50 mL of test fluid at approximately 0.5 mL/sec to the center of the specimen via a calibrated Eppendorf pipet. A representative example of the NMR Amplitude versus time graph is shown in FIG. 5.

Figure 4B:
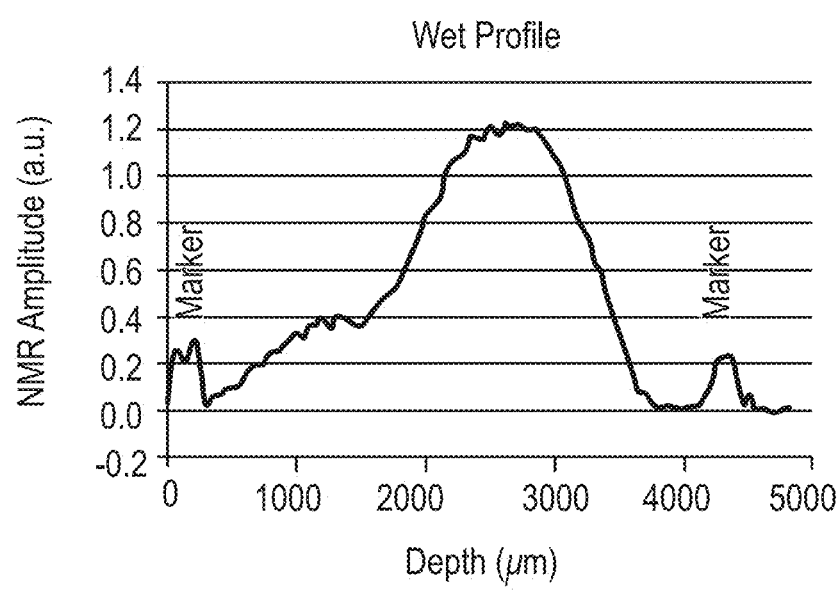

The third measurement is a 1-D Wet Distribution Profile Immediately after the Kinetic measurement is complete, replace the cap on the specimen. The Wet Distribution is run under the same experimental conditions as the previous Dry Distribution, described above. A representative graph is shown in FIG. 4B.

Calibration of the NMR Amplitude for the Kinetic signal can be performed by filling glass vials (8 mm outer diameter and a defined inner diameter by at least 50 mm tall) with the appropriate fluid. Set the instrument conditions as described for the kinetics experiment. A calibration curve is constructed by placing an increasing number of vials onto the instrument (vials should be distributed equally over the 40 mm×40 mm measurement region) and perform the kinetic measurements. The volumes are calculated as the summed cross sectional area of the vials present multiplied by the z-resolution where Resolution (mm) is calculated as 1/Acquisition Time (s) divided by the instruments Gradient Strength (Hz/mm) The Calibration of the NMR Amplitude for the Distribution Profile is performed as an internal calibration based on the dry and wet profiles. In this procedure the area beneath wet and dry profile were calculated and after subtracting them the total area (excluding markers) was obtained. This total area is correlated to the amount of applied liquid (here 1.5 mL). The liquid amount (μL) per 100 μm step can then be calculated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent product comprising a topsheet, a backsheet, and an absorbent core, the absorbent core comprising an absorbent structure comprising a nonwoven acquisition stratum comprising enrobeable fibers overlying a storage stratum comprising an open cell HIPE foam, wherein a transition zone is exhibited between the acquisition stratum and the storage stratum, wherein the transition zone exhibits a slope that is negative on a plot having the Position in microns on an X axis wherein the bottom of the substrate is plotted closest to the origin and top is plotted furthest away and wherein the NMR signal is on the Y axis when analyzed using the Kinetics and ID Liquid Distribution by NMR-MOUSE test protocol, after the second of two 0.5 ml fluid insults over two 5 minute test periods.

2. The absorbent product of claim 1, wherein the fibers have an average thickness, as measured per SEM, ca. between 100 and 600 um.

3. The absorbent product of claim 1, wherein the smooth transition zone comprises pores having an average diameter between 20 micron and 60 micron.

4. The absorbent product of claim 3, wherein the smooth transition zone comprises pores having an average diameter between 30 micron and 40 micron.

5. The absorbent product of claim 1, wherein the smooth transition zone to caliper ratio is between 0.1 and 0.4.

6. The absorbent product of claim 1, wherein the ratio of the Capillary Work Potential of the topsheet to the Capillary Work Potential to the absorbent structure is below 1.4.

7. The absorbent product of claim 3, wherein the ratio of the basis weight of the fibers to the basis weight of the open-cell foam is below 0.48.

8. The absorbent product of claim 3, wherein the open-cell foam comprises an average cell size above 20 micron and a basis weight above 110 gsm.

9. The absorbent product of claim 1, wherein the smooth transition zone comprises a heterogeneous mass comprising a portion of the HIPE foam formed about and enrobing a plurality of the enrobeable fibers.

10. The absorbent product of claim 1, wherein the nonwoven acquisition stratum and the storage stratum have been ring-rolled together.

11. The absorbent product of claim 9 comprising a plurality of discrete pieces of HIPE foam each formed about and enrobing a plurality of the enrobeable fibers.

* * * * *